(12) United States Patent
Oppenheimer et al.

(10) Patent No.: US 11,390,587 B2
(45) Date of Patent: Jul. 19, 2022

(54) PREPARATION OF SULFONAMIDE HERBICIDE PROCESS INTERMEDIATES

(71) Applicant: Corteva Agriscience LLC, Indianapolis, IN (US)

(72) Inventors: Jossian Oppenheimer, Midland, MI (US); Matthias S. Ober, Midland, MI (US); Mark E. Ondari, Freeland, MI (US); Michael Gullo, Midland, MI (US); Jayachandran Devaraj, Zionsville, IN (US); Amaruka Hazari, Carmel, IN (US); Will Kruper, Midland, MI (US)

(73) Assignee: Corteva Agriscience LLC, Indianapolis, IN (US)

( * ) Notice: Subject to any disclaimer, the term of this patent is extended or adjusted under 35 U.S.C. 154(b) by 0 days.

(21) Appl. No.: 17/296,675

(22) PCT Filed: Dec. 20, 2019

(86) PCT No.: PCT/US2019/067737
§ 371 (c)(1),
(2) Date: May 25, 2021

(87) PCT Pub. No.: WO2020/139740
PCT Pub. Date: Jul. 20, 2020

(65) Prior Publication Data
US 2022/0041554 A1 Feb. 10, 2022

Related U.S. Application Data

(60) Provisional application No. 62/835,689, filed on Apr. 18, 2019, provisional application No. 62/806,176, filed on Feb. 15, 2019, provisional application No. 62/785,343, filed on Dec. 27, 2018.

(51) Int. Cl.
*C07D 213/70* (2006.01)
*C07C 323/27* (2006.01)

(52) U.S. Cl.
CPC .......... *C07D 213/70* (2013.01); *C07C 323/27* (2013.01)

(58) Field of Classification Search
CPC ............................. C07D 231/70; C23C 323/27
See application file for complete search history.

(56) References Cited

U.S. PATENT DOCUMENTS

| 5,858,924 A * | 1/1999 | Johnson | A01N 47/24 504/241 |
| 2005/0215570 A1 * | 9/2005 | Hamilton | C07D 487/04 514/259.31 |

FOREIGN PATENT DOCUMENTS

| CN | 108 707 109 A | 10/2018 |
| WO | 98/13367 A1 | 4/1998 |
| WO | 2005/063780 A1 | 7/2005 |
| WO | PCT/US19/67737 | 3/2020 |

* cited by examiner

*Primary Examiner* — Timothy R Rozof

(57) ABSTRACT

Improved methods for preparing chemical precursors to sulfonyl chloride III, which are important intermediates in the preparation of pyroxsulam herbicide are provided. Specifically, these precursors are compounds of Formulas VII and/or VIII, and IX, wherein R is a $C_1$-$C_6$ alkyl, $R^1$ is a $C_1$-$C_6$ alkyl, X is Cl or OH, Y is halogen, OH, or $OR^2$, and $R^2$ is a $C_1$-$C_6$ alkyl.

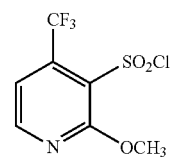

III

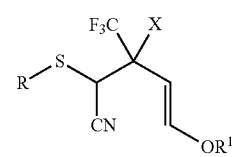

VII

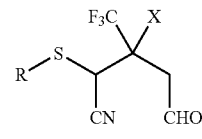

VIII

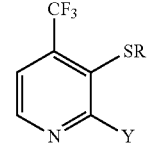

IX

27 Claims, 3 Drawing Sheets

PREPARATION OF SULFONAMIDE HERBICIDE PROCESS INTERMEDIATES

This application is the National Stage Entry of International Application No. PCT/US19/67737, filed on Dec. 20, 2019, which claim the benefit of priority of U.S. Provisional Application Ser. No. 62/785,343, filed on Dec. 27, 2018, to U.S. Provisional Application Ser. No. 62/806,176, filed on Feb. 15, 2019, to U.S. Provisional Application Ser. No. 62/835,689, filed on Apr. 18, 2019, the entire disclosures of which are each hereby expressly incorporated by reference.

BACKGROUND

Pyroxsulam (I), a member of the triazolopyrimidine sulfonamide family of herbicides, which is disclosed in WO2002036595, is a commercially available herbicide that offers control of many broadleaf and grass weeds in cereal crops. The preparation of pyroxsulam has been described in various references, such as in United States Patent Application Publication No. 2005/0215570, the disclosure of which is incorporated by reference herein.

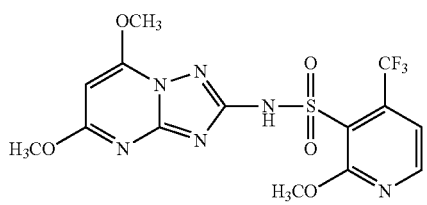

I

The final step in the preparation of pyroxsulam (I) involves coupling the amine of Formula II with the sulfonyl chloride of Formula III:

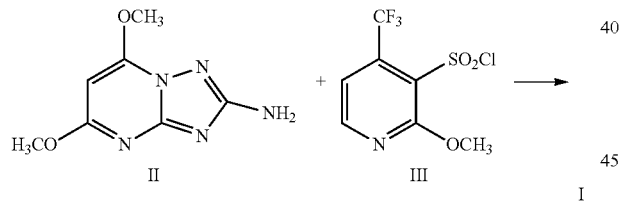

I

Sulfonyl chloride III was prepared by converting the 2-oxo-pyridine IIIa, via the 2-chloropyridine IIIb, into the 2-methoxypyridine IIIc. Sulfonyl chloride III was then prepared by metalation/thiolation of IIIc with a mixture of lithium diisopropylamide (LDA) and elemental sulfur, followed by chloroxidation of the resulting lithiothiolate with chlorine/HCl to provide III.

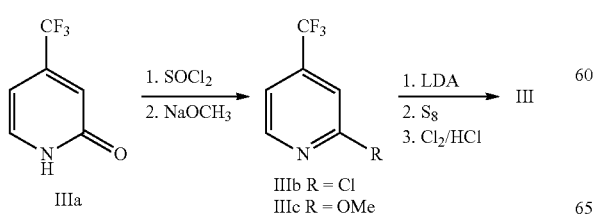

However, such conventional methods can be costly, reducing the profit, and in some cases may adversely affect the ability to use the produced pyroxsulam in some markets.

A need therefore exists to reduce the cost of the manufacture of pyroxsulam in an efficient and economic manner. Also, there is a need for the ability to make pyroxsulam in a manner that allows it to be sold in currently restricted markets.

SUMMARY

Described herein are improved methods for preparing chemical precursors of sulfonyl chloride III, which are important intermediates in the preparation of pyroxsulam herbicide. Specifically, these precursors are compounds of Formulas VII and/or VIII and IX, wherein R is a $C_1$-$C_6$ alkyl, $R^1$ is a $C_1$-$C_6$ alkyl, X is Cl or OH, Y is halogen, OH, or $OR^2$, and $R^2$ is a $C_1$-$C_6$ alkyl.

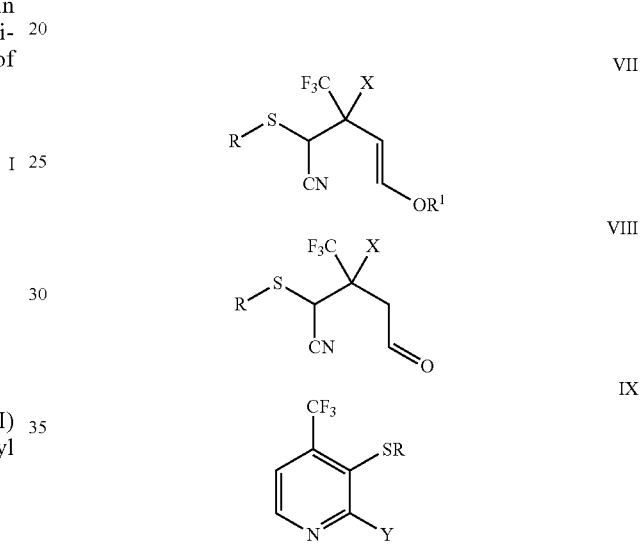

Another aspect of the present disclosure are the novel intermediates produced by the described methods, viz., the compounds:

a)

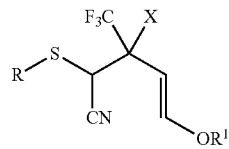

wherein R is a $C_1$-$C_6$ alkyl, $R^1$ is a $C_1$-$C_8$ alkyl, and X is Cl or OH; and b)

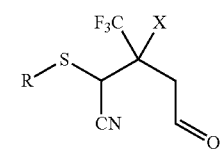

wherein R is a $C_1$-$C_6$ alkyl, $R^1$ is a $C_1$-$C_8$ alkyl, and X is Cl or OH; and c)

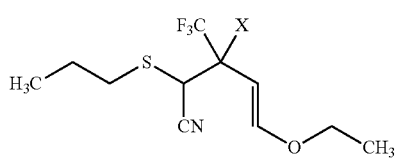

wherein X is Cl or OH.

BRIEF DESCRIPTION OF THE DRAWINGS

The above mentioned and other features and objects of this disclosure, and the manner of attaining them, will become more apparent and the disclosure itself will be better understood by reference to the following description of exemplary aspects of the disclosure taken in conjunction with the accompanying drawings, wherein.

Figure 1:
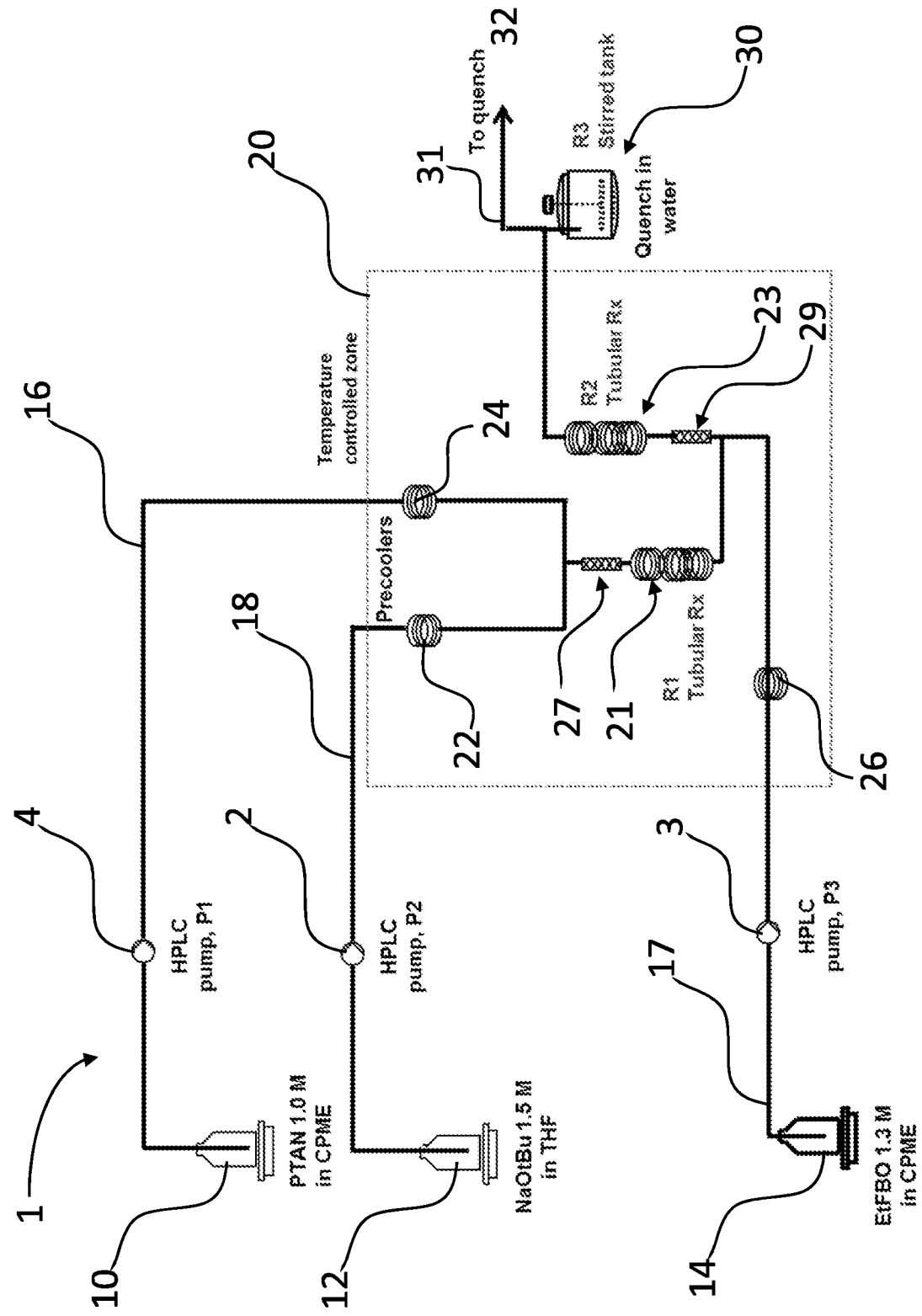
FIG. 1 is a schematic diagram of an exemplary continuous flow reactor for the synthesis of (E)-5-ethoxy-3-hydroxy-2-(propylthio)-3-(trifluoromethyl)pent-4-enenitrile according to various aspects.

Corresponding reference characters indicate corresponding parts throughout the several views. Although the drawings represent aspects of the present disclosure, the drawings are not necessarily to scale and certain features may be exaggerated in order to better illustrate and explain the present disclosure. The exemplification set out herein illustrates exemplary aspects of the disclosure, in various forms, and such exemplifications are not to be construed as limiting the scope of the disclosure in any manner.

DETAILED DESCRIPTION

Methods of preparing precursors of sulfonyl chloride III, which can be an important intermediate in the preparation of pyroxsulam herbicide, are described. Specifically, these precursors are compounds of Formulas VII and/or VIII, and IX, wherein R is a $C_1$-$C_6$ alkyl, $R^1$ is a $C_1$-$C_8$ alkyl, X is Cl or OH, Y is halogen, OH, or $OR^2$, and $R^2$ is a $C_1$-$C_6$ alkyl.

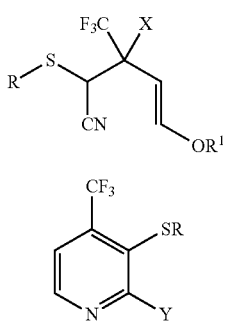

As illustrated in Schemes 1 and 2 described herein, these methods can include chemical process steps that: (1) convert compounds of Formulas IV, and V or VI, into the nitrile of Formula VII and/or VIII, and (2) convert VII and/or VIII into the compound of Formula IX, wherein Y is halogen, OH, or $OR^2$, and $R^2$ is a $C_1$-$C_6$ alkyl, by use of Reactants A, B, C, D or E, which include an acid (Reactant A), an alcohol (Reactant B), water (Reactant C), an alkoxide (Reactant D), or a dehydrative halogenating reagent (Reactant E), and combinations thereof.

Scheme 1

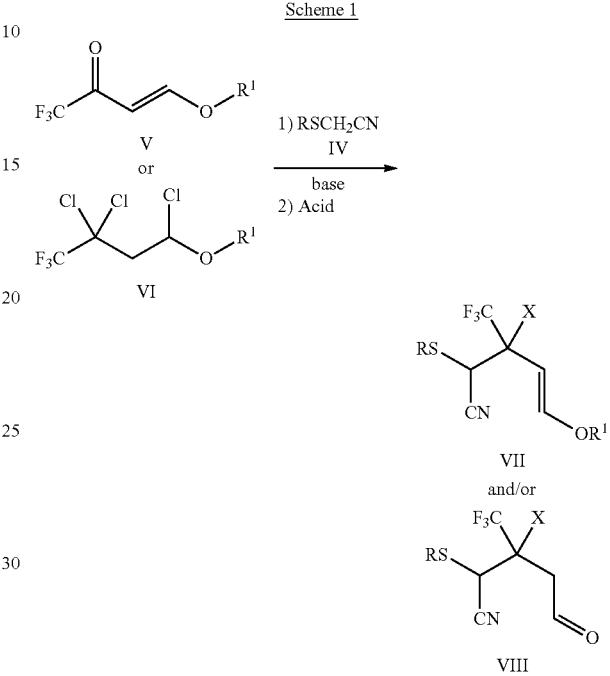

wherein R is a $C_1$-$C_6$ alkyl, $R^1$ is a $C_1$-$C_8$ alkyl and X is Cl or OH;

Scheme 2

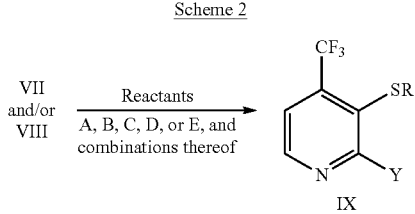

wherein R is a $C_1$-$C_6$ alkyl, Y is halogen, OH, or $OR^2$, and $R^2$ is a $C_1$-$C_6$ alkyl.

I. Definitions

The term "halo" or "halogen" as used herein may be understood to include one or more of F, Cl, Br, and I.

As used herein, the term "aryl," as well as derivative terms such as aryloxy, may be understood to include groups that include a monovalent aromatic carbocyclic group of from 6 to 14 carbon atoms. Aryl groups can include a single ring or multiple condensed or fused rings. In some aspects, aryl groups include $C_6$-$C_{10}$ aryl groups.

Examples of aryl groups include, but are not limited to, phenyl, biphenyl, naphthyl, tetrahydronaphthyl, phenylcyclopropyl, and indanyl. In some aspects, the aryl group can be a phenyl, indanyl or naphthyl group. The term "heteroaryl", as well as derivative terms such as "heteroaryloxy", may be understood to include a 5-membered or 6-membered aromatic ring containing one or more heteroatoms, e.g., N, O or S. In some aspects, these heteroaromatic rings may be fused to other aromatic systems. In some aspects, the heteroaryl group can be a pyridyl, pyrimidyl or a triazinyl group. The aryl or heteroaryl substituents may be unsubstituted or substituted with one or more chemical moieties. Examples of suitable substituents include, for example, amino, halo, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_{10}$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_4$ alkyl, $C_1$-$C_{10}$ alkoxycarbonyl and $C_1$-$C_4$ haloalkyl.

II. Preparation of Nitrile VII (and/or Aldehyde VIII)

In some aspects, the first step of the method to prepare the compounds of Formula IX, wherein Y is halogen, OH, or $OCH_3$, may involve the conversion of the compound of Formula V or VI into the nitrile of Formula VII and/or VIII, by reaction of V or VI with a metal anion of alkylthioacetonitrile IV (M is Li, Na or K), prepared as exemplified in Scheme 3. Bases for use in this reaction step may include, but are not limited to, organolithium reagents such as n-butyllithium, sec-butyllithium, lithium diisopropylamide (LDA), and lithium or sodium hexamethyldisilazane (LHMDS or NaHMDS). Other bases such as sodium and potassium tert-butoxides (Na-tBuO and K-tBuO), and sodium and potassium tert-amyloxides can also be used. The reaction of V with lithioacetonitrile has been disclosed in U.S. Pat. No. 8,063,226, the disclosure of which is included by reference herein, whereas use of V or VI to make VII (X=Cl or OH) has not been previously disclosed. The reaction is quenched with an acid. Acids for use in this reaction step may include, but are not limited to, mineral acids such as hydrochloric acid (HCl), phosphoric acid ($H_3PO_4$) or sulfuric acid ($H_2SO_4$), or organic acids such as acetic acid. In some aspects a buffered system may be used, for example in the formation of the compound of Formula VII may be accomplished in a buffered system. Exemplary buffers can be phosphate buffers, Tris buffers, sodium acetate buffers, ammonium acetate buffers, tartrate buffers, citrate buffers, or combinations thereof.

Scheme 3

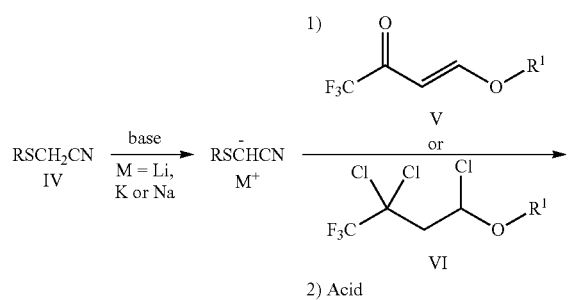

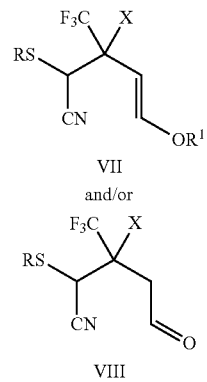

wherein R is a $C_1$-$C_6$ alkyl, R is a $C_1$-$C_8$ alkyl and X is Cl or OH;

Compound VI can be made by the following process as described in WO2002053518, the disclosure of which is incorporated by reference herein.

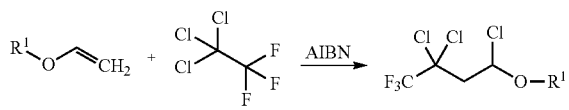

The process step to make VII (and/or VIII) can be conducted in solvents such as, but not limited to, ether solvents like THF (tetrahydrofuran), DME (1,2-dimethoxyethane), 2-methyl-THF, diethyl ether, cyclopentylmethyl ether (CPME), or dioxane, and mixtures thereof, and mixtures of the ether solvents with hydrocarbon solvents such as pentane, hexane, cyclohexane, toluene, and the like or use of the hydrocarbon solvent alone. The temperature range for conducting this process step may be done at relatively low temperatures as little as about −80° C., −75° C., −70° C., −60° C., −50° C., or −45° C., or at temperatures as high as about −30° C., −25° C., −20° C., −10° C., 0° C., 10° C., or 25° C., or any range defined between any two of the foregoing values, such as about −80° C. to about 25° C., about −80° C. to about 0° C., about −70° C. to about −30° C., about −50° C. to about −25° C., about −75° C. to about −25° C., for example.

Also, in various aspects, the reaction may be conducted over various periods of time, such as short as about 15 minutes, 30 minutes, 45 minutes, 1 hour, or as long as about 2 hours, 24 hours, 36 hours, or 72 hours, or any range defined between any of the foregoing values, such as about 15 minutes to about 72 hours, about 30 minutes to about 36 hours, about 45 minutes to about 24 hours, about 1 hour to about 24 hours, or about 15 minutes to about 2 hours, for example.

In some aspects, excess molar amounts may be used to completely react one of the reagents. In some aspects, the molar equivalent of reagents may have a ratio as little as about 1, 1.01, 1.05, 1.07, 1.1, as high as ratios of about 1.15, 1.2, 1.3, or 1.5, or any range defined between any pair of the foregoing values, such as molar equivalents of the base can be used in the process to make VII (and/or VIII) in ratios between about 1 to about 1.5, between about 1.01 to about 1.15, between about 1.1 to about 1.15, about 1.05 to about 1.3, or between about 1.1 to about 1.5, for example.

The process step to make VII (and/or VIII), as shown in Scheme 3, can be conducted in a batch process mode (e.g., individual batches of product are prepared), a semi-batch mode, semi-continuous, or in a continuous process mode (e.g., a flow process).

In the continuous process mode, reactants 2-(propylthio)acetonitrile and (E)-4-ethoxy-1,1,1-trifluorobut-3-en-2-one are premixed in Solvent 1 to form Solution 1, which is then connected to Pump 1 (P1). The base is dissolved in Solvent 1 to form Solution 2 which is connected to Pump 2 (P2). The acid is dissolved in THF or CPME to form Solution 3 which is connected to Pump 3 (P3). Solution 1 (containing the reactants) and Solution 2 (containing the base) are precooled and mixed together through a tee junction into a static mixer in Reactor 1 (R1). The mixture after spending the required residence time in R1 is then mixed together with a precooled acid quench solution (Solution 3) via a tee junction at the eye of the static mixer in reactor 2 (R2). The exit of R2 was connected to a product collection tank. At completion of the continuous flow process run, the organic solution in the product collection tank is further processed by employing standard isolation and purification techniques so that the desired products may be obtained. Bases for use in the continuous flow process include t-amyloxide, sodium tert-butoxide, potassium tert-butoxide, or NaHMDS (same bases as the batch process), and solvents may include THF, CPME, or toluene.

In another aspect of a continuous process mode setup, reactants 2-(propylthio)acetonitrile and (E)-4-ethoxy-1,1,1-trifluorobut-3-en-2-one are separate solution in Solvent 1 to form Solution 1 and 2, Solution 1 is then connected to Pump 1 (P1). (E)-4-ethoxy-1,1,1-trifluorobut-3-en-2-one dissolved in solvent 1 to make Solution 2 which is connected to Pump. The base is dissolved in Solvent 1 to form Solution 3 which is connected to Pump 2 (P2). The acid is dissolved in THF or CPME to form Solution 4 which is connected to Pump 4 (P4). Solution 1 (containing 2-(propylthio)acetonitrile) and Solution 3 (containing the base) are precooled and mixed together through a tee junction into a static mixer in Reactor 1 (R1). The mixture after spending the required residence time in R1 is then mixed together with a precooled Solution 2 containing (E)-4-ethoxy-1,1,1-trifluorobut-3-en-2-one via a tee junction at the eye of the static mixer in reactor 2 (R2). The mixture, after spending a residence time (t) in R2, is then mixed together with a precooled acid quench solution (Solution 4) via a tee junction at the eye of the static mixer in reactor 3 (R3). The exit of R3 was connected to a product collection tank. At completion of the continuous flow process run, the organic solution in the product collection tank is further processed by employing standard isolation and purification techniques so that the desired products may be obtained. Bases for use in the continuous flow process include t-amyloxide, sodium tert-butoxide, potassium tert-butoxide, or NaHMDS (same bases as the batch process), and solvents may include THF, CPME, or toluene.

III. Preparation of Substituted Pyridines IX

The next step of the method to prepare the compound of Formula IX involves the conversion of the compound of Formula VII, wherein R is a $C_1$-$C_6$ alkyl, $R^1$ is a $C_1$-$C_6$ alkyl and X is Cl or OH, to the substituted pyridine of Formula VIII (Scheme 4) by treatment with a reactant or a combination of reactants. The reactant or reactant combination used must include a reactant that promotes cyclization of nitrile VII to pyridine VIII.

Scheme 4

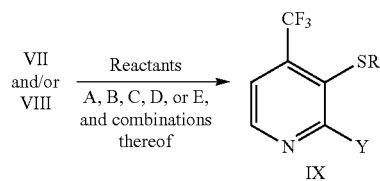

wherein R is $C_1$-$C_6$ alkyl, Y is halogen, OH, or $OR_2$, and $R_2$ is $C_1$-$C_6$ alkyl;

Table 1 lists a number of exemplary reactants that may be used for the transformation shown in Scheme 4. Reactants A (an acid) or E (a dehydrative halogenating reagent) readily promote the cyclization of VII (and/or VIII) to IX, however, in some aspects, the use of reactants B, C, or D alone or in combination may not readily promote cyclization of VII (and/or VIII) to IX. However, in various aspects when reactants B, C or D are used in combination with reactants A or B, either in a simultaneous manner (mixed together prior to addition to VII and/or VIII) or a sequential manner (added separately to VII and/or VIII), then cyclization of nitrile VII and/or VIII to pyridine IX may occur.

TABLE 1

Descriptions of Reactants A-E

| Reactant | Generic Name | Generic Reactants | Specific Reactants | Promotes Cyclization VII/VIII to IX |
|---|---|---|---|---|
| A | acid | $H_2Y$, HY | $H_2SO_4$, HCl, HBr | yes |
| B | alcohol | $C_1$-$C_6$ alcohol | MeOH, EtOH | no |
| C | water | water | water | no |
| D | alkoxide | MOR, where R = $C_1$-$C_6$ alkyl, and M = Na, K | NaOMe, KOMe | no |
| E | dehydrative halogenating reagent | $SOY_2$, $POY_3$, $PY_3$, $PY_5$ | $SOCl_2$, $SOBr_2$, $POCl_3$, $PCl_3$, oxalyl chloride | yes |

In some aspects conducted in a simultaneous manner, a mixture containing an acid and an alcohol was combined with compound VII and/or VIII to provide compound IX, wherein X is Cl or OH, R is $C_1$-$C_6$ alkyl, $R^1$ is a $C_1$-$C_6$ alkyl, and $R_2$ is $C_1$-$C_6$ alkyl. This may be illustrated by the following reaction:

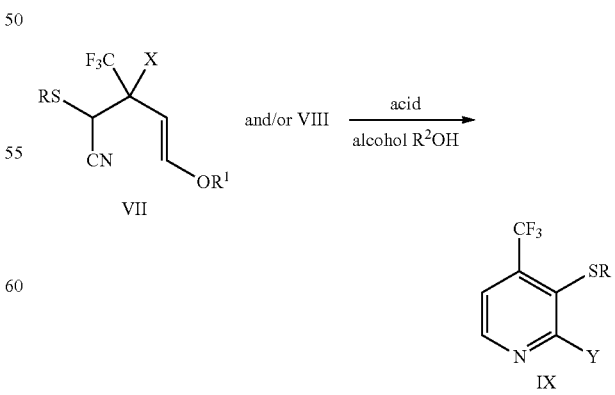

In various aspects, in a somewhat similar manner, a mixture containing an acid and water can be combined with compound VII and/or VIII to provide compound IX, wherein X is Cl or OH, R is $C_1$-$C_6$ alkyl, and $R^1$ is a $C_1$-$C_6$ alkyl. These aspects are illustrated by the following reaction:

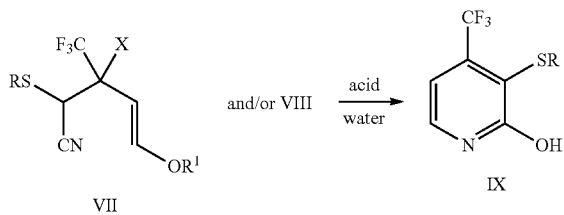

In some aspects conducted in a sequential manner, an anhydrous acid HY (Y is Cl or Br) can be combined with compound VII and/or VIII to provide compound IX, wherein R is $C_1$-$C_6$ alkyl, and Y is Cl or Br, which can then be combined with an alkoxide $MOR^2$ (M is Na or K) to provide compound IX wherein R is $C_1$-$C_6$ alkyl and $R^2$ is $C_1$-$C_6$ alkyl. This may be illustrated by the following exemplary reactions:

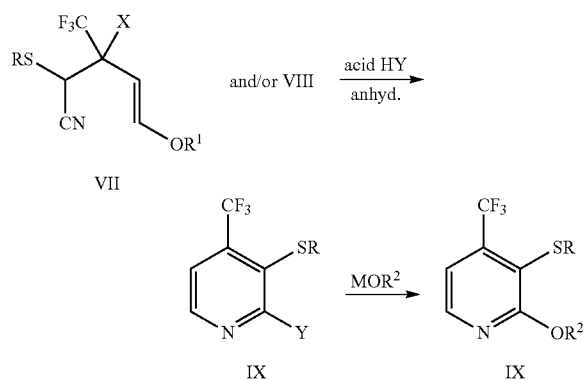

In some aspects, conducted in a sequential manner, a dehydrative halogenating reagent ($SOY_2$, $POY_3$, $PY_3$, $PY_5$ or oxalyl chloride) can be combined with compound VII and/or VIII to provide compound IX, wherein R is $C_1$-$C_6$ alkyl, and Y is Cl or Br, which can then be further combined with an alkoxide $MOR^2$ (M is Na or K) to provide compound IX wherein R is $C_1$-$C_6$ alkyl, and $R^2$ is $C_1$-$C_6$ alkyl. This can be exemplified or illustrated by the following reactions:

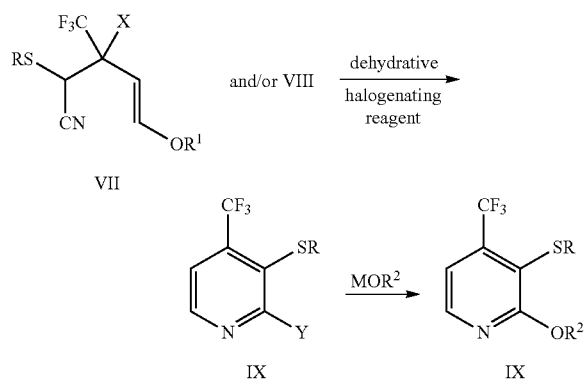

Solvents that may be suitable for use in the preparation of the substituted pyridines of Formula IX from the compounds of Formula VII and/or VIII include, but are not limited to, acetonitrile (ACN), N,N-dimethylformamide (DMF), dichloromethane (DCM), 1,2-dichloroethnae (DCE), tetrahydrofuran (THF), 2-methyl-THF, dioxane, cyclopentyl methyl ether (CPME), toluene, one or more xylenes, methanol, or ethanol, and mixtures thereof.

In some aspects or aspects, the reactant or reactants may also serve as the solvent in the preparation of the substituted pyridines of Formula IX.

The preparation of the compound of Formula IX from the compound of Formula VII and/or VIII may be conducted at a temperature of at least about 0° C., at least about 10° C., at least about 20° C., at least about 25° C., at least about 30° C., at least about 40° C., at least about 50° C., at least about 60° C., at least about 70° C., at least about 80° C., at least about 90° C., or at least about 100° C. In some aspects, the preparation of the compound of Formula IX from the compound of Formula VII and/or VIII may be conducted at a temperature from about 0° C. to about 50° C., from about 10° C. to about 50° C., from about 25° C. to about 50° C., from about 25° C. to about 60° C., from about 25° C. to about 70° C., from about 25° C. to about 80° C., from about 25° C. to about 90° C., from about 25° C. to about 100° C., from about 25° C. to about 125° C., or from about 25° C. to about 150° C.

IV. Preparation of 2-alkoxy-4-(trifluoromethyl)pyridine-3-sulfonyl Halides

The compound of Formula IX, wherein R is a $C_1$-$C_6$ alkyl, and $R^2$ is a $C_1$-$C_6$ alkyl, can be converted to the compound of Formula IIId utilizing a previous disclosed method. This conversion is shown in Scheme 5 and involves treating compound IX with a hydrohalide acid HY, a halogen $Y_2$, and water, wherein Y is Cl or Br, to provide the compound of Formula IIId, wherein Y is Cl or Br, and $R^2$ is a $C_1$-$C_6$ alkyl.

Scheme 5

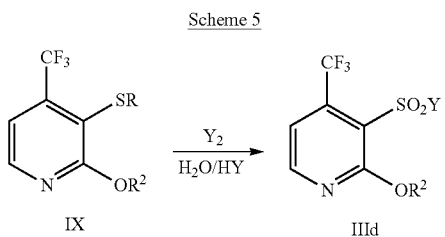

wherein R is $C_1$-$C_6$ alkyl, $R^2$ is $C_1$-$C_6$, and Y is Cl or Br.

In one aspect of the method to prepare the compound of Formula III, $Y^2$ is $Cl_2$ (chlorine), the hydrohalide acid HY is HCl, and $R^2$ is $CH_3$.

In another aspect of the method to prepare the compound of Formula IIId, a water immiscible co-solvent is included. This co-solvent may be selected from dichloromethane, 1,2-dichloroethane, chlorobenzene, 1,2-dichlorobenzene, chloroform, trichlorobenzene, or α,α,α-trifluorotoluene, and mixtures thereof.

In another aspect of the method to prepare the compound of Formula III, a phase transfer catalyst may be included. Suitable phase transfer catalysts to include are the tetraalkylammonium halides and tetraalkylammonium sulfates such as, for example, methyl tributylammonium chloride, tetrabutylamonnium halide (chloride or bromide) or tetrabutyl ammonium sulfate.

In another aspect of the method to prepare the compound of Formula III, a solution of sodium chloride, such as a saturated solution, can be used as the aqueous phase for the reaction.

In yet another aspect of the method to prepare the compound of Formula III, a catalytic acid, such as trifluoroacetic acid, may be used to promote the reaction.

The preparation of the compound of Formula III from the compound of Formula IX may be conducted at a temperature from about −5° C. to about 40° C., from about 0° C. to about 40° C., from about 0° C. to about 30° C., from about 0° C. to about 20° C., from about 0° C. to about 15° C., from about 0° C. to about 10° C., or from about 0° C. to about 5° C.

V. Isolation/Purification

After preparation of the compounds of Formulas III, VII and/or VIII and IX by the methods described herein, the products may be isolated by employing standard isolation and purification techniques. For example, the crude product may be isolated using standard methods as described herein and purified by crystallization using a single solvent or a mixture of two or more solvents. Also, the crude product may be purified by washing it with, or stirring it in, a one, two or three-component solvent mixture. In one aspect, the crude product may be purified by stirring it in an aqueous alcohol solvent mixture.

The crude product may also be purified by dissolving it in one solvent to form a solution and then adding a second solvent to the solution to cause the product to crystallize out of the mixture of the two solvents.

The crude product may also be purified by any known separation means, such as by distillation (e.g., distillation under a vacuum).

The following examples are presented to illustrate the methods and compositions described herein.

EXAMPLES

Example 1A. Preparation of 2-(propylthio)acetonitrile

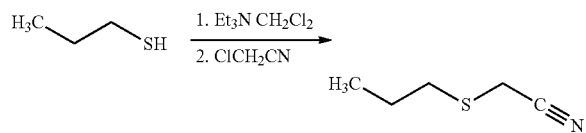

Into a 250-mL 3-neck round bottom flask (with thermal well) was charged dichloromethane (DCM; 200 ml) and the mixture was cooled with water/ice bath. The flask was then charged with propane-1-thiol (29.3 ml, 315 mmol) and the flask was briefly padded with nitrogen using a glass bubbler with an outlet to a bleach (5% v/v in water) scrubber. The clear solution was allowed to stir until the internal temperature stabilized (4° C.) after which triethylamine (47.9 ml, 344 mmol) was added over 5 minutes using an addition funnel (the internal temperature increased to 6° C.); the addition funnel was rinsed with about 5 mL of DCM. The mixture was allowed to stir until the internal temperature stabilized at 4° C. after which 2-chloroacetonitrile (21.62 g, 286 mmol) was added slowly over 10 min using an addition funnel. (Even though this funnel had been rinsed with DCM after being used to transfer triethylamine, a dark layer of oil was observed on top of chloroacetonitrile (some fumes were briefly observed inside the addition funnel). The internal temperature increased slowly to 19° C. within the course of the addition. After addition was complete, the reaction mixture slowly turned from clear (with a tint of brown) to cloudy; it was stirred for about 30 min after which time the temperature had decreased to 16° C. and white precipitate had formed (stirring was unimpeded). The flask was taken out of the ice bath and an aliquot (2 mL) was removed by syringe, washed with water, dried, concentrated (1.3 g clear oil) and analyzed by 1H NMR analysis which showed about 10% conversion). The reaction temperature slowly increased to 32° C. within 30 minutes of taking the flask out of the ice bath after which it decreased to room temperature (21° C.) within 20 minutes. The reaction mixture was stirred at this temperature for another 2.5 h after which an aliquot (0.3 mL) was taken, filtered, concentrated and analyzed by 1H NMR which showed about 99% conversion of chloroacetonitrile to the product. The reaction mixture was filtered under gentle vacuum using a disposable filter and the filtrate (200 mL, slightly yellowish-brown) was concentrated under reduced pressure and the resulting slurry (small amount of solids had crashed out) was distilled under vacuum using a short-path distillation head with water cooling. Three distillates were collected (25 g total, 75% yield, 98-99% purity by 1H NMR. 1H NMR (400 MHz, Chloroform-d) δ 3.30 (s, 2H), 2.79-2.65 (m, 2H), 1.69 (h, J=7.3 Hz, 2H), 1.03 (t, J=7.3 Hz, 3H). 13C NMR (101 MHz, Chloroform-d) δ 116.67, 34.58, 21.99, 16.92, 13.20.

Example 1b. Preparation of PTAN

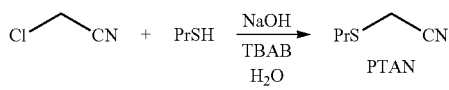

Pr = propyl group

A 2 L jacketed glass reactor was connected to an overhead stirrer (set at 350 rpm) and was loaded with NaOH (50% wt/wt in water, 612.0 g, 7.68 mol; Fisher) followed by deionized water (600.3 g, 33.35 mol) and catalytic tetrabutylammonium bromide (TBAB, 50% wt/wt in water; 52.4 g, 0.08 mol; Sachem Inc.). The reactor contents were cooled to 20° C. internal temperature after which propanethiol (464.50 g, 6.10 mol, Sigma Aldrich) was added using a peristaltic pump at a rate of about 10 g/min (starting temperature 19.5° C.; end temperature 20.7° C.). The jacket temperature was set to 2° C. and the reaction mixture was stirred for 1 h 45 min after which chloroacetonitrile (456.70 g, 6.05 mol; Sigma Aldrich) was added using a peristaltic pump at a rate of about 3 g/min. The start temperature was 2.5° C. and initially increased at about 0.3° C./min for the first about 50 g of PrSH; about 0.2° C./min for the next 100 g of PrSH, and 0.05° C./min thereafter with the end temperature of 20.5 C. The reaction mixture was left to cool down to 2° C. and stirred at that temperature overnight after which agitation was stopped and the aqueous layer was drained. Note: The reaction does not need to stir overnight. The reaction should be done in less than 11 h. The reaction is monitored by NMR. The resulting oil was washed with sodium bicarbonate solution (200 g) to give about 665 g of clear oil (about 96% yield, about 97% pure by NMR) of the crude product. This material was purified via distillation using a short path distillation head. The material was loaded to the distillation pot, placed under vacuum, and heated slowly. The vacuum pump used for the distillation held relatively constant vacuum normally between 1.0-3.0 torr. Distillation of PTAN at this pressure typically occurred between 85° C. to 91° C. If sufficient water was left in the material from the reaction conditions an azeotrope was noticed to collect in the receiving flask at temperatures ranging from approximately 70° C. to 85° C., which was distilled under vacuum to give 627 g (90% yield, about 99% pure by NMR). 1H NMR (400 MHz, Chloroform-d) δ 3.30 (s, 2H), 2.79-2.65 (m, 2H), 1.69 (h, J=7.3 Hz, 2H), 1.03 (t, J=7.3 Hz, 3H). 13C NMR (101 MHz, Chloroform-d) δ 116.67, 34.58, 21.99, 16.92, 13.20.

Example 1c. Preparation of 5-ethoxy-3-hydroxy-2-(propylthio)-3-(trifluoromethyl)pent-4-enenitrile Via Batch Process

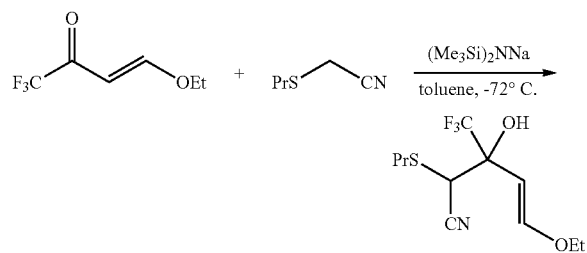

A 250-mL 3-neck round bottom flask containing a stir bar was charged with sodium bis(trimethylsilyl)amide (4.97 g, 27.1 mmol) and toluene (68 ml) and the mixture was stirred until the solids dissolved (slightly yellow clear solution). The flask was padded with nitrogen with stirring and then immersed in a dry ice/isopropanol bath and cooled until the internal temperature reached –72° C. Into this solution was added a solution of 2-(propylthio)acetonitrile (2.6 g, 22.57 mmol) in toluene (12 mL) by syringe over 20 min while maintaining the internal temperature at below –65° C. To this solution was added neat (E)-4-ethoxy-1,1,1-trifluorobut-3-en-2-one (4.17 g, 24.83 mmol) by syringe over 20 min. The reaction mixture was thereafter quenched with phosphoric acid (5% v/v in water). The organic layer was dried with MgSO4 and purified by flash column chromatography (220 g 'Gold' column) using EtOAc/hexanes (0-50% v/v) as the eluent to give 5-ethoxy-3-hydroxy-2-(propylthio)-3-(trifluoromethyl)pent-4-enenitrile (4.5 g, 15.88 mmol, 70.4% yield) as a mixture of two diastereomers (orange-yellow oil). 1H NMR: (400 MHz, Chloroform-d) δ 6.88 ((d, J=12.5 Hz) and 6.86 (d, J=12.4 Hz), 1H), 4.92 ((d, J=12.5 Hz) and 4.87 (d, J=12.6 Hz), 1H), 3.31 ((s) and 3.28 (s), 1H), 2.88-2.68 (m, 2H), 1.81-1.56 (m, 2H), 1.32 (td, J=7.0, 0.7 Hz, 3H), 1.04 (td, J=7.4, 1.9 Hz, 3H). 13C NMR: (101 MHz, Chloroform-d) δ 153.51, 152.74, 125.44, 125.39, 122.59, 122.55, 115.52, 115.47, 96.24, 95.58, 77.23, 76.12, 75.83, 75.54, 75.29, 75.00, 65.88, 65.80, 41.21, 40.62, 35.22, 35.12, 22.51, 22.24, 14.46, 14.43, 13.17. 19F NMR: (376 MHz, Chloroform-d) δ –77.84, –78.95.

Example 1d. Preparation of 5-ethoxy-3-hydroxy-2-(propylthio)-3-(trifluoromethyl)pent-4-enenitrile Via a Continuous Flow Process

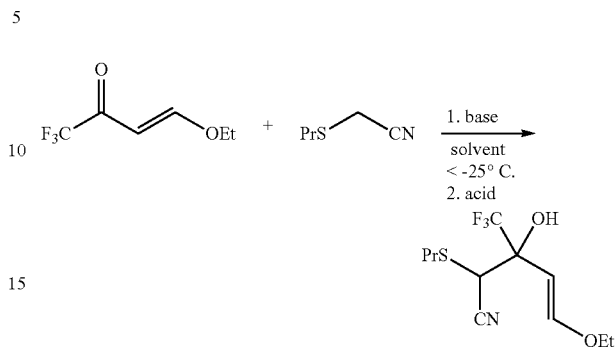

A solution of 2-(propylthio)acetonitrile and (E)-4-ethoxy-1,1,1-trifluorobut-3-en-2-one are premixed in Solvent 1 to form Solution 1 which is connected to Pump 1 (P1). The base is dissolved in Solvent 1 to form Solution 2 which is connected to Pump 2 (P2). The acid is dissolved in THF or CPME to form Solution 3 which is connected to Pump 3 (P3). All three pumps are Lab Alliance dual-head HPLC pumps (piston-type). Solution 1 (containing the reactants) and Solution 2 (containing the base) are precooled via heat exchangers and mixed together through a tee junction into a static mixer in Reactor 1 (R1). The mixture after spending the required residence time in R1 is then mixed together with precooled acid quench solution (Solution 3) (delivered from heat exchanger) via a tee junction at the eye of the static mixer in reactor 2 (R2). The exit of R2 is connected through a back-pressure controller to the product collection tank. At completion of the continuous flow process run, the organic solution in the product collection tank is assayed by quantitative HPLC analysis to determine the yield of the product. Bases for use in the continuous flow process include t-amyloxide, sodium tert-butoxide, potassium tert-butoxide, or NaHMDS and solvents may include THF, CPME, or toluene, and mixtures thereof.

Example 1d. An Additional Preparation of 5-ethoxy-3-hydroxy-2-(propylthio)-3-(trifluoromethyl)pent-4-enenitrile

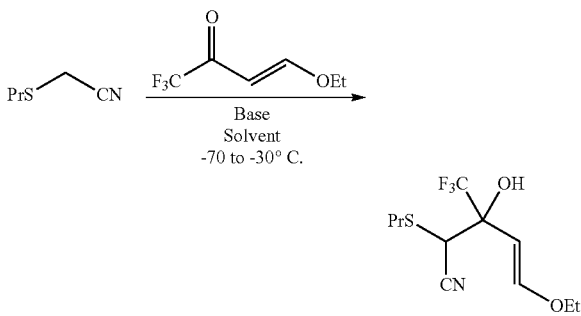

To a dry and inerted with nitrogen 1 L jacketed reactor (Reactor 1) with an overhead mechanical stirrer 29.03 grams of solid sodium t-butoxide ((292.99 mmol, 1.35 eq, white powder, fine grained, 97 wt % purity) was loaded. The reactor was re-inerted with nitrogen and 597.3 g of CPME was loaded using a peristaltic pump. The 4.63 wt % solution of sodium t-butoxide was chilled to approximately −71.0° C. Using a peristaltic pump, 25.0 g of neat PTAN (217 mmol, limiting reagent) was added over about 15 min to Reactor 1 to furnish the PTAN anion solution. The addition rate was such that the reaction temperature of the reactor was maintained below −69° C. In a separate vessel was prepared a 37 wt % solution of ETFBO (48.9 g, 282.14 mmol, 1.3 equiv. 97 wt % purity) in CPME. This solution was continuously added to Reactor 1 using a peristaltic pump over about 40 minutes to afford the alkoxide solution. The line was flushed with 65 g of CPME. The addition rate was such that the reaction temperature of the reactor was maintained below −66° C. The product of the reaction (alkoxide) was transferred immediately by gravity into a 2 L jacketed reactor with an overhead mechanical stirrer containing a pre-cooled aqueous solution of 1.62 equivalents of potassium phosphate monobasic (1 Molal, pH=4.5), internal temperature at 0°. The 2 L jacketed reactor contents were warmed to 25° C. The aqueous phase was decanted and the organic phase analyzed by LC and NMR. The organic phase was used in the next step as a crude solution.

Example 2a. Synthesis of 2-chloro-3-(propylthio)-4-(trifluoromethyl pyridine

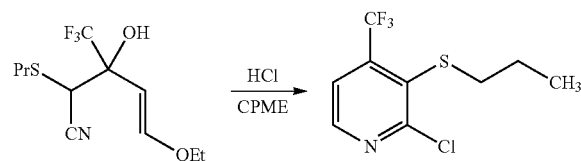

Into a 50 mL 1-neck round bottom flask equipped with stir bar was added (E)-5-ethoxy-3-hydroxy-2-(propylthio)-3-(trifluoromethyl)pent-4-enenitrile (1 g, 3.53 mmol, nitrogen atmosphere). While stirring, anhydrous hydrochloric acid in cyclopentyl methyl ether (CPME, 3M) (20.00 ml, 60.0 mmol, 17.0 equiv. of HCl) was added and the reaction stirred for three days at RT. TLC analysis (20% ethyl acetate in hexane) indicated complete conversion. The reaction mixture was worked up by careful addition into 100 mL of a stirred, concentrated aqueous sodium bicarbonate solution. Additional bicarbonate solution was added until no more gas development was observed and the water phase tested slightly basic. The organic phase was separated, and the aqueous phase extracted twice with ethyl acetate. The combined organic phases were dried over magnesium sulfate, concentrated on the rotary evaporator and further dried under high vacuum until a constant weight was achieved. The residue was analyzed by 1H NMR without further workup. Crude 2-chloro-3-(propylthio)-4-(trifluoromethyl) pyridine was received in form of a yellow oil with a purity of approximately 88%. (0.9057 g, 3.12 mmol, 88% yield, corrected for NMR purity).

An analytically pure sample was obtained by stirring 50 mg (176 μmol) of the starting material with HCl in CPME (3M, 1 mL, 3 mmol, 17 eq HCl) for two days, followed by heating to 70° C. in a 4 mL screw cap vial for two hours. Extractive bicarbonate/ethyl acetate workup was performed described above. No further purification was necessary. Chromatograms and spectra of the thereby received crude material are shown below. 1H NMR (400 MHz, CDCl$_3$) δ 8.49 (dq, J=5.0, 0.8 Hz, 1H), 7.54 (d, J=5.0 Hz, 1H), 2.95 (t, J=7.3 Hz, 2H), 1.63 (h, J=7.3 Hz, 2H), 1.02 (t, J=7.3 Hz, 3H); 13C NMR (101 MHz, CDCl$_3$) δ 159.10, 149.24, 144.77 (q, J=30.8 Hz), 130.62, 121.95 (q, J=275.0 Hz), 119.56 (q, J=5.1 Hz), 37.89, 22.92, 13.34. 19F NMR (376 MHz, CDCl$_3$) δ −61.66; Low resolution ESI(+), expected for [C$_9$H$_{10}$ClF$_3$NS]+: m/z=256.0 (35Cl) and 258.0 (37Cl), found: m/z: 255.8, 257.9, 296.8 (MeCN adduct), 298.8 (MeCN adduct).

Example 2b. Preparation of 2-chloro-3-(propylthio)-4-(trifluoromethyl)pyridine

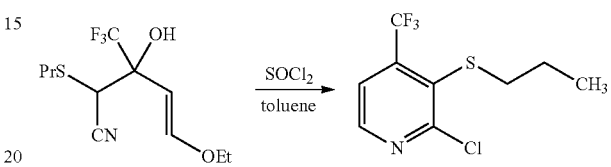

Method 1: Under nitrogen atmosphere, into a 4 mL vial was added 5-ethoxy-3-hydroxy-2-(propylthio)-3-(trifluoromethyl)pent-4-enenitrile (50 mg, 0.176 mmol) and dry toluene (0.5 mL), followed by thionyl chloride (38.6 μl, 0.529 mmol). The mixture was stirred for 1 h, after which ethanol (30 μL was added). The reaction was stirred for two days.

For HPLC analysis, a 400 μL aliquot of the reaction mixture was taken and diluted with a 1:2 mixture of water and acetonitrile to a total volume of 3 mL. From this diluted mixture, a 240 μL aliquot (about 0.4 mg) were transferred to a self-filtering HPLC filter vial, diluted with 150 μL of acetonitrile and 10 μL of acetic acid/triethylamine 1:1:buffer. Low resolution ESI(+), expected for [C$_9$H$_{10}$ClF$_3$NS]+: m/z=256.0 (35Cl) and 258.0 (37Cl), found: m/z: 255.8, 257.9, 296.8 (MeCN adduct), 298.8 (MeCN adduct).

Method 2: Under nitrogen atmosphere, into a 4 mL vial was added of 5-ethoxy-3-hydroxy-2-(propylthio)-3-(trifluoromethyl)pent-4-enenitrile (50 mg, 0.176 mmol), followed by thionyl chloride (502 μl, 6.88 mmol). The reaction was stirred for two days. The reaction was worked up dropwise addition to with saturated sodium bicarbonate solution (1 mL) to which sodium hydroxide (50% w/w) was added dropwise up to the point until the mixture turned basic. The mixture was extracted with ethyl acetate. A sample from the ethyl acetate layer was diluted into 400 μL of acetonitrile and 10 μL of acetic acid/triethylamine buffer to a concentration of approximately 1 mg/mL (based on starting material), micro-filtered and analyzed by LC/MS. Low resolution ESI(+), expected for [C$_9$H$_{10}$ClF$_3$NS]+: m/z=256.0 (35Cl) and 258.0 (37Cl), found: m/z: 255.8, 257.9, 296.8 (MeCN adduct), 298.8 (MeCN adduct).

Example 2c. Preparation of 2-ethoxy-3-(propylthio)-4-(trifluoromethyl)pyridine

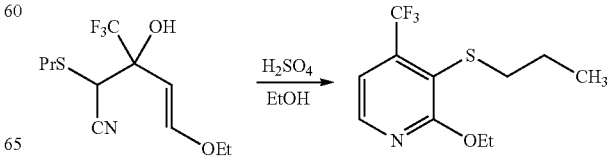

5-Ethoxy-3-hydroxy-2-(propylthio)-3-(trifluoromethyl)pent-4-enenitrile (50 mg, 0.176 mmol) was added to a 4 mL vial with stir bar, followed by ethanol (30 μL) and concentrated sulfuric acid (198 μL, 3.71 mmol). The reaction was stirred at RT overnight, and then heated to 80° C. for 4 hours. The content of the vial was worked up by dropwise addition to concentrated sodium bicarbonate solution and extraction with methylene chloride. The organic phase was separated, concentrated and dried under high vacuum. The product 2-ethoxy-3-(propylthio)-4-(trifluoromethyl)pyridine was isolated as a dark residue: 30 mg, 0.113 mmol, (64%); 1H NMR (400 MHz, CDCl$_3$) δ 8.47 (d, J=4.7 Hz, 1H), 6.49 (d, 4.7 Hz, 1H), 4.74-4.39 (m, 2H), 3.35-3.07 (m, 2H), 1.77-1.56 (m, 2H), 1.31 (t, J=7.5 Hz, 3H), 1.07 (td, J=7.4, 3H); 19F NMR (376 MHz, CDCl$_3$) δ −59.6; 13C NMR (101 MHz, CDCl$_3$) δ 170.0, 158.4, 144.3 (t, J=31.3 HZ), 122.2 (q, J=275.2), 104.2 (q, J=4.65), 85.2, 40.2, 33.1, 18.7, 12.8, 9.9; MS (ESI−) m/z=235.9 (M−H+); MS (ESI+) m/z=237.9 (M+H+).

Example 2d. Preparation of 2-methoxy-3-(propylthio)-4-(trifluoromethyl)pyridine

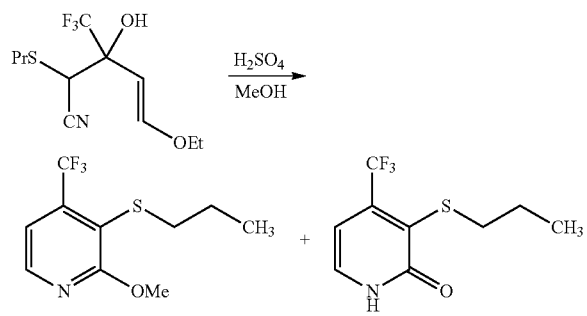

5-Ethoxy-3-hydroxy-2-(propylthio)-3-(trifluoromethyl)pent-4-enenitrile (50 mg, 0.176 mmol) was added to a 4 mL vial with stir bar, followed by methanol (30 μL) and concentrated sulfuric acid (198 μL, 3.71 mmol) and then heated at 60° C. overnight. The contents of the vial were worked up by dropwise addition to concentrated sodium bicarbonate solution and extraction with methylene chloride. The organic phase was separated, concentrated and dried under high vacuum. A darkly colored residue was received (approximately 32 mg) that contained the desired product 2-methoxy-3-(propylthio)-4-(trifluoromethyl)pyridine [MS (ESI+) m/z=251.9 (M+H+)] in a mixture with 3-(propylthio)-4-(trifluoromethyl)pyridin-2(1H)-one [MS (ESI−) m/z=235.9 (M−H+), MS (ESI+) m/z=237.9 (M+H+)] and a further unidentified impurity.

Example 3a. Preparation of 2-methoxy-4-(trifluoromethyl)pyridine-3-sulfonyl chloride

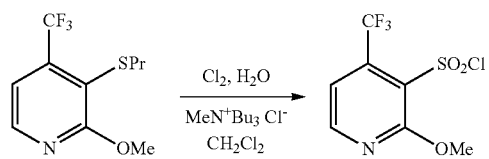

A 125-mL flat bottomed 3-neck jacketed reactor (propylene glycol/water bath fluid) was equipped with mechanical stirring (PTFE half-moon stir paddle). The jacket temperature was set to 0° C. and charged with 2-methoxy-3-(propylthio)-4-(trifluoromethyl)pyridine (13.93 mmol) dissolved in 66.3 g methylene chloride, followed by a solution of methyl tributylammonium chloride (0.641 mmol) in water (25 g). Stirring was initiated (330 rpm) and when the reaction mixture reached the desired temperature, chlorine addition was started. Chlorine (125.9 mmol) was added over 125 minutes. After approximately 0.3 g chlorine was added, a white slurry formed which gradually thinned as the addition progressed, and became increasingly yellow in color. At the end of the chlorine addition, all solids had dissolved. Throughout the addition, the reaction temperature was maintained below 2.5° C. HPLC analysis at the end of the chlorine addition indicated 73.8 area % of the desired product. The reaction was sampled after 1, 2, and 3 hours, with a maximum of 75.5 area % desired product at the 1 hour sampling. Excess chlorine was quenched with 4.62 g of 40% aqueous sodium bisulfite solution. The reaction mixture was transferred to a separatory funnel. The organic phase was cut and concentrated by rotary evaporation to yield 4.28 g of a colorless oil, 76.0 area % desired product by HPLC analysis.

As previously described, in various aspects the synthesis of (E)-5-ethoxy-3-hydroxy-2-(propylthio)-3-(trifluoromethyl)pent-4-enenitrile may be performed. For example, as shown in Scheme A below.

Scheme A

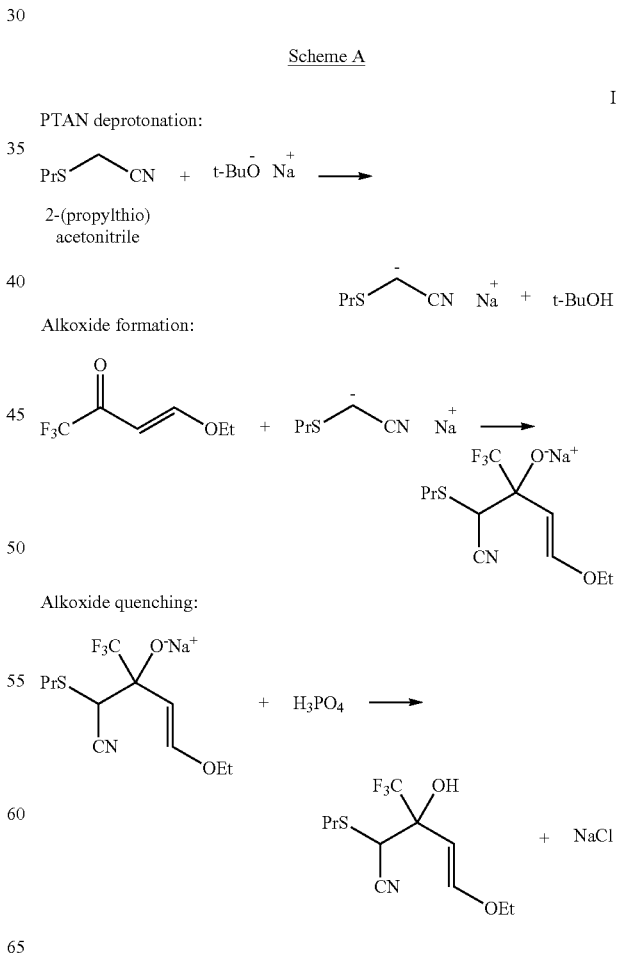

In various aspects, the various synthesis processes may be done in a batch, semi-continuous, or continuous reactor.

Figure 2:
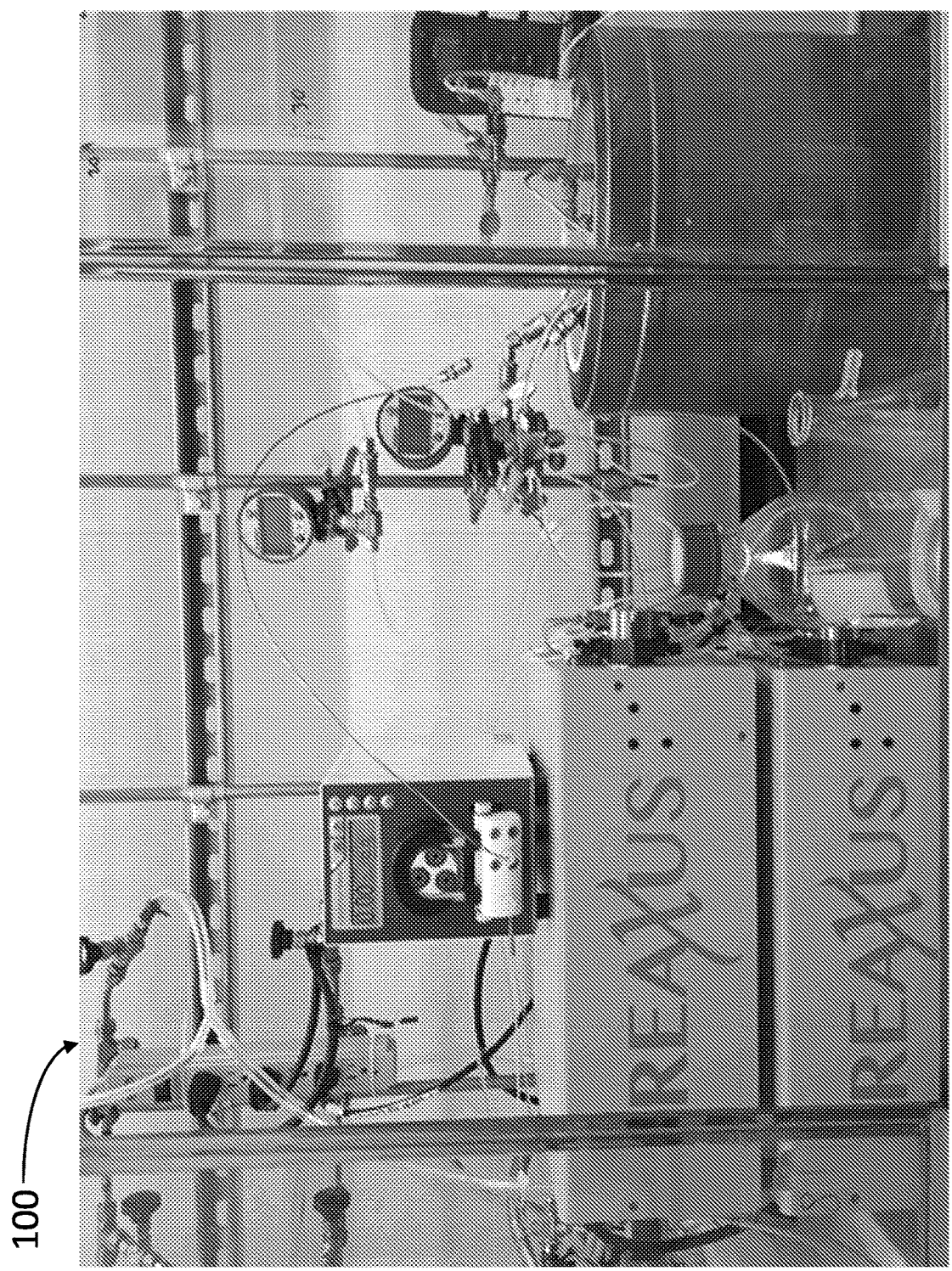
FIG. 2 is an a picture of a pilot continuous flow reactor according to various aspects.
Figure 3:
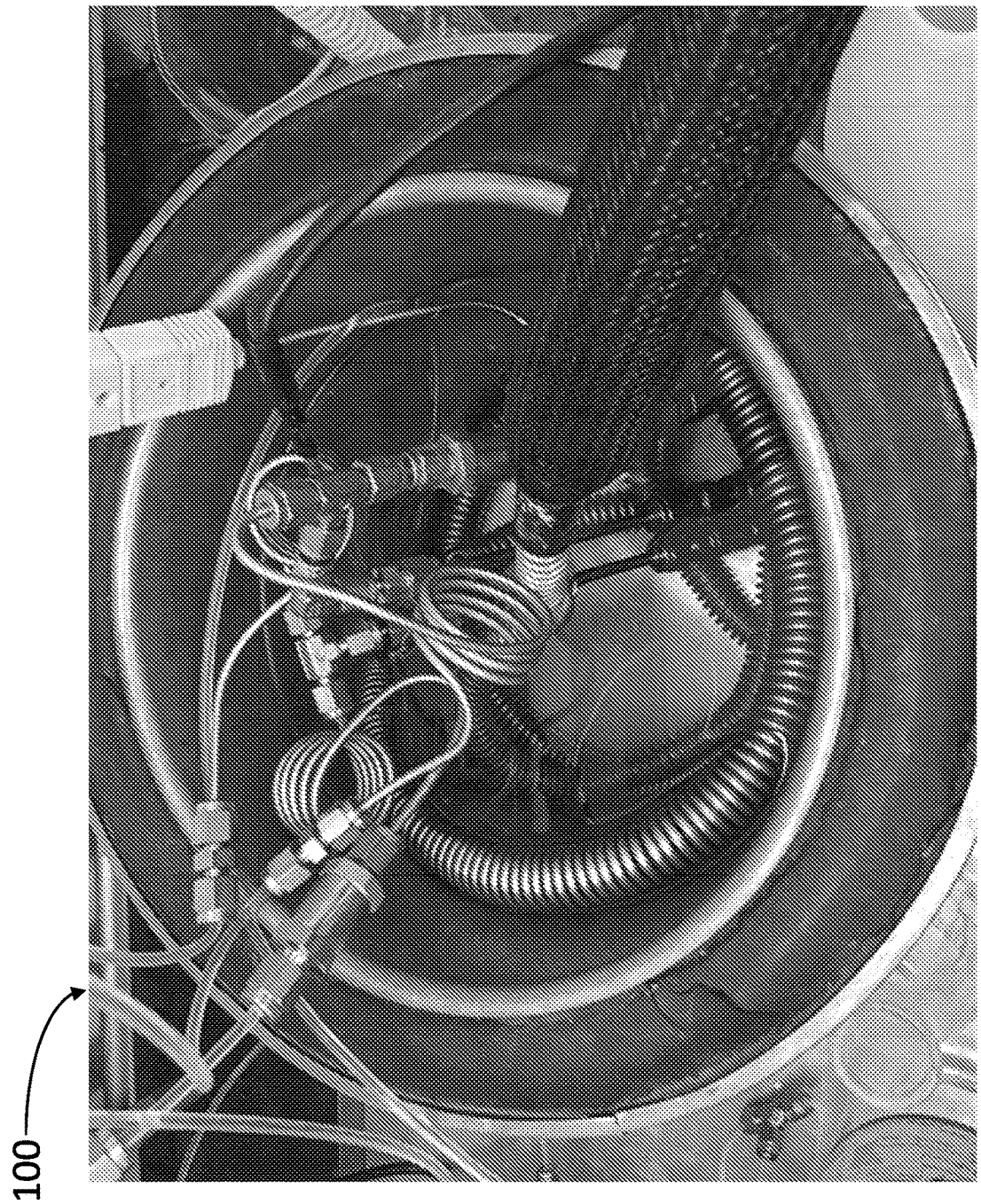
FIG. 3 is an a picture of a continuous stirred tank with a water quench of a pilot continuous flow reactor according to various aspects.

With reference to FIG. 1, an exemplary semi-batch reactor flow-diagram 1 is shown. FIGS. 2 and 3 show an exemplary pilot semi-batch reactor 100 according to various aspects. In accordance with the exemplary aspect shown in FIG. 1, 2(propylthiol) acetonitrile (PTAN) deprotonation was performed in the first tubular reactor 21 using 1.5 eq. of base. This is followed by alkoxide formation in the second tubular reactor 23 using 1.3 eq. of ETFBO. The alkoxide was then quenched with a proton source in a jacketed stirred tank reactor 30. The two tubular reactors 21 and 23 were operated at −20° C. and the stirred tank reactor 30 was operated at 0° C. The residence time for the deprotonation and alkoxide reactors, 21 and 23, was 0.5 minutes and 0.33 minutes respectively. The stirred tank reactor 30 was operated as semi-batch to make a predetermined amount of product for downstream testing. The alkoxide can also be quenched in a third tubular reactor (not shown) using a proton source at 0 to 20° C.

The reaction sequence in Scheme A was previously demonstrated in batch mode at −78° C. with about 83% yield in 2-4 gram scale. In various aspects, the use of a continuous flow system, the reaction can be performed at higher temperatures such as −20° C. with yields up to 90-92%. In various aspects, the short residence time may help enable a smaller reactor volume which may help with chemical inventory, foot-print and potentially capital expenditures. As reactions of this type may be scaled to larger quantities, certain aspects can account for the maintenance of low temperatures, which can lead to longer reaction times (slower addition of reagents), local hot spots, and/or deeper cryogenic condition. In some aspects, longer reaction times may lead to an increased impurity formation and reduced yield. In some aspects, the use of cryogenic conditions also adds expense to a manufacturing process and not many CROs and 3PMs are equipped to handle cryogenic conditions.

The reactors were assembled as shown in FIGS. 2 and 3. Pump 1 (P1) 4 is connected to PTAN bottle, Pump 2 is connected to base solution bottle and Pump 3 is connected to the ETFBO. All three pumps are dual acting piston pumps. P1 and P2 outlets are precooled to the reactor temperature, mixed via a 'tee' connections (not shown) and immediately enters a helical type static mixer (3/16" OD, 12 elements) 27. The downstream of the static mixer is connected to a coiled reactor (⅛" OD, 16' length tube coiled to give a OD of 2"). Reactor 1 outlet joins with the precooled stream of ETFBO from P3 through a similar 'tee'/static mixer assembly 27 and enters Reactor 2 (23). Reactor 2 (23) has the same geometry as the Reactor 1 (21). A K type thermocouple is installed at Reactor 2 (23) outlet to measure the reactor outlet temperature. Reactor 2 (23) outlet has the option to be diverted either to a waste/sample collection or product collection. The product collection is done via a 1 liter jacketed stirred tank (R3) (30) with known amount of quench solution and running the flow reactor for a prescribed amount of time. The flow reactor outlet emerges from the −20° C. bath and enters the stirred tank through a dip-tube. The dip-tube is positioned in such a way that alkoxide solution enters in the aqueous phase and bubbles through the aqueous phase to the organic phase. The reactors and the precoolers 22, 24, and 26 of FIG. 1 were placed in a cooling bath as shown in FIG. 2. The jacketed reactor was connected to a circulating bath.

Prior to the reaction, THF was pumped through the reactors to flush the system. Once the temperature reached the desired level while pumping solvents, the flow was diverted to reacting reagents from bottles. Flow rates were: P1=13.2 mL/min for the PTAN solution, P2=13.2 mL/min for base solution and P3=13.2 mL/min for the EtFBO solution. The reactors R1 and R2, and pre-cooler loops were maintained at −20° C. The stirred tank was maintained at 0° C. For the reactor configuration and flow rates mentioned above, the residence time in R1 was 0.5 minutes and in R2 was 0.33 minutes. Samples were collected at different time points indicated in Table 2 below and analyzed by 19F NMR and HPLC to determine conversion to the desired product. Once the samples show that the reactors had reached steady state, the reactor effluent is diverted to the stirred tank where the quench solution is kept at 0° C. under agitation.

TABLE 2

| Exp. # | RT1 | RT2 | T | NaOtBu eq. | EtFBO eq. | Yield |
|---|---|---|---|---|---|---|
| A1 | 0.25 | 0.17 | −35° C. | 1.5 | 1.3 | 89.6% |
| A5 | 0.5 | 0.34 | −35° C. | 1.5 | 1.3 | 87.7% |
| A6 | 1 | 0.67 | −35° C. | 1.5 | 1.3 | 85.7% |
| B1 | 0.5 | 0.33 | −20° C. | 1.5 | 1.3 | 90.6% |
| C1 | 0.5 | 0.33 | −25° C. | 1.5 | 1.3 | 92.0% |

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various aspects, the terms "consisting essentially of" and "consisting of" can be used in place of "comprising" and "including" to provide for more specific aspects of the invention and are also disclosed.

What is claimed is:
1. A method comprising
   combining a compound of Formula IV, a first base, and a compound of Formula V or Formula VI, and mixtures thereof,

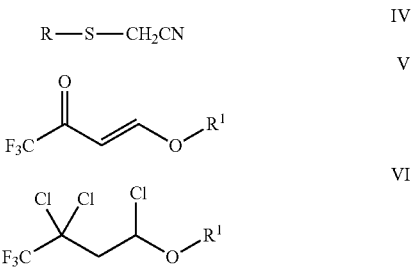

to form the compound of Formula VII, the compound of Formula VIII, or a mixture thereof,

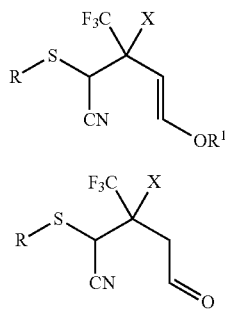

wherein R is a $C_1$-$C_6$ alkyl, $R^1$ is a $C_1$-$C_6$ alkyl, and X is Cl or OH.

2. The method of claim 1, further comprising preparing the compound of Formula IV by a method by combining an alkyl mercaptan RSH, a haloacetonitrile Y—$CH_2CN$, and a second base, wherein R is a $C_1$-$C_6$ alkyl, and Y is a halogen.

3. The method of claim 1, further comprising combining the compound of Formula VII or Formula VIII, or mixtures thereof, wherein R is a $C_1$-$C_6$ alkyl, $R^1$ is a $C_1$-$C_6$ alkyl, and X is Cl or OH, with a reactant selected from an acid, an alcohol, water, an alkoxide, or a dehydrative halogenating reagent, and combinations thereof to form a compound of Formula IX

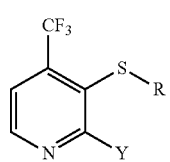

wherein R is a $C_1$-$C_6$ alkyl, and Y is a halogen, OH, or $OR^2$, wherein $R^2$ is a $C_1$-$C_6$ alkyl.

4. The method of claim 3, wherein the acid is $H_2SO_4$, HCl, HBr, HI or p-toluenesulfonic acid.

5. The method of claim 3, wherein the alcohol is a $C_1$-$C_6$ alcohol.

6. The method of claim 3, wherein the alkoxide is a $C_1$-$C_6$ sodium or potassium alkoxide.

7. The method of claim 3, wherein the dehydrative halogenating reagent is $SOCl_2$, $SOBr_2$, $POCl_3$, $POBr_3$, $PCl_3$, $PBr_3$, $PCl_5$ or $PBr_5$, or oxalyl chloride, and combinations thereof.

8. The method of claim 3, wherein the alcohol is methanol.

9. The method of claim 3, wherein the alkoxide is sodium methoxide or potassium methoxide.

10. The method of claim 3, wherein the combining includes the simultaneous combination of the acid and the alcohol with the compound of Formula VII or Formula VIII, or mixtures thereof, to provide the compound of Formula IX wherein R is a $C_1$-$C_6$ alkyl, and Y is $OR^2$, wherein $R^2$ is a $C_1$-$C_6$ alkyl.

11. The method of claim 3, a wherein the combining includes the simultaneous combination of the acid and water with the compound of Formula VII or Formula VIII, and mixtures thereof, to provide the compound of Formula IX wherein R is a $C_1$-$C_6$ alkyl, and Y is OH.

12. The method of claim 3, wherein the combining includes the sequential combination of an acid that is HCl or HBr, and then the alkoxide with the compound of Formula VII or Formula VIII, and mixtures thereof, to provide the compound of Formula IX wherein R is a $C_1$-$C_6$ alkyl, and Y is $OR^2$, wherein $R^2$ is a $C_1$-$C_6$ alkyl.

13. The method of claim 3, wherein the combining includes the sequential combination of the dehydrative halogenating reagent and then the alkoxide with the compound of Formula VII or Formula VIII, and mixtures thereof, to provide the compound of Formula IX wherein R is a $C_1$-$C_6$ alkyl, and Y is $OR^2$, wherein $R^2$ is a $C_1$-$C_6$ alkyl.

14. The method of claim 3, further comprising combining the compound of Formula IX, wherein R is a $C_1$-$C_6$ alkyl, and Y is OH, with a dehydrative halogenating reagent that is thionyl chloride to form the compound of Formula IX, wherein R is a $C_1$-$C_6$ alkyl, and Y is Cl.

15. The method of claim 3, further comprising combining the compound of Formula IX, wherein R is a $C_1$-$C_6$ alkyl, and Y is halogen, with sodium methoxide or potassium methoxide to form the compound of Formula IX, wherein R is a $C_1$-$C_6$ alkyl, and Y is $OCH_3$.

16. The method of claim 3, further comprising combining the compound of Formula IX, wherein R is a $C_1$-$C_6$ alkyl, and Y is $OCH_3$, with chlorine and water to form the compound of Formula III

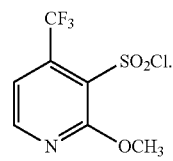

17. The method of claim 1, wherein the first base is selected from the group including n-butyllithium, sec-butyllithium, lithium diisopropylamide (LDA), lithium hexamethyldisilazane (LiHMDS), sodium hexamethyldisilazane (NaHMDS), sodium tert-butoxide (Na-tBuO), potassium tert-butoxide (K-tBuO), sodium tert-amyloxide, or potassium tert-amyloxide, or mixtures thereof.

18. The method of claim 1, further comprising a solvent selected from the group including THF (tetrahydrofuran), DME (1,2-dimethoxyethane), 2-methyl-THF, diethyl ether, cyclopentylmethyl ether (CPME), dioxane, pentane, hexane, cyclohexane, or toluene, or mixtures thereof.

19. The method of claim 1, wherein the combining is conducted at 25° C. to about −80° C.

20. The method of claim 1, wherein the method is conducted as a batch process.

21. The method of claim 1, wherein the method is conducted as a continuous process.

22. A compound comprising:

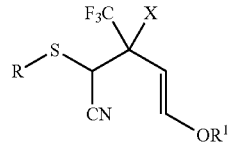

wherein R is a $C_1$-$C_6$ alkyl, $R^1$ is a $C_1$-$C_6$ alkyl, and X is Cl or OH.

23. The method of claim 3, further comprising combining the compound of Formula IX, wherein R is a $C_1$-$C_6$ alkyl, and Y is $OCH_3$, with a solution of sodium chloride to form the compound of Formula III

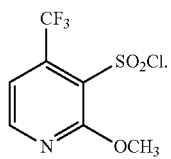

III

24. The method of claim 23, wherein the solution of sodium chloride is saturated.

25. The method of claim 3, further comprising adding trifluoroacetic acid to promote a reaction to form the compound of Formula III

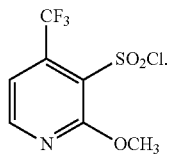

III

26. A compound comprising:

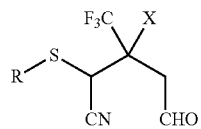

wherein R is a $C_1$-$C_6$ alkyl and X is Cl or OH.

27. A compound comprising:

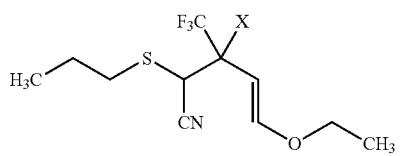

wherein X is Cl or OH.

* * * * *